(12) United States Patent
Robert et al.

(10) Patent No.: US 8,992,695 B2
(45) Date of Patent: Mar. 31, 2015

(54) WASHER CHAMBER PRESSURE-RELIEF ASSEMBLY

(75) Inventors: Maxime Robert, Quebec (CA); Claude Gravel, Quebec (CA)

(73) Assignee: STERIS, Inc., Temecula, CA (US)

( * ) Notice: Subject to any disclaimer, the term of this patent is extended or adjusted under 35 U.S.C. 154(b) by 802 days.

(21) Appl. No.: 13/170,743

(22) Filed: Jun. 28, 2011

(65) Prior Publication Data
US 2011/0315171 A1    Dec. 29, 2011

Related U.S. Application Data

(60) Provisional application No. 61/359,511, filed on Jun. 29, 2010.

(51) Int. Cl.
| F16K 17/18 | (2006.01) |
| F16K 17/19 | (2006.01) |
| B08B 3/02 | (2006.01) |
| A61L 2/26 | (2006.01) |

(52) U.S. Cl.
CPC . *F16K 17/18* (2013.01); *A61L 2/26* (2013.01); *F16K 17/19* (2013.01); *B08B 3/02* (2013.01)
USPC .................................................. 134/115 R

(58) Field of Classification Search
CPC ........ F16K 17/94; F16K 17/196; F16K 17/26
USPC ....... 134/115 R; 137/14, 493.1, 493.3, 493.4, 137/493.7
See application file for complete search history.

(56) References Cited

U.S. PATENT DOCUMENTS

| 3,699,999 | A |  | 10/1972 | Dunkelis ................... 137/493.4 |
| 4,515,179 | A |  | 5/1985 | Edmunds et al. ........ 137/543.13 |
| 5,226,442 | A | * | 7/1993 | Taylor .............................. 137/70 |
| 5,307,831 | A |  | 5/1994 | McNeely ........................ 137/14 |
| 8,171,954 | B2 |  | 5/2012 | Hancock et al. ......... 137/543.13 |
| 2004/0074538 | A1 |  | 4/2004 | Ortenzi et al. ............ 137/493.4 |
| 2004/0215170 | A1 | * | 10/2004 | Phung et al. .................. 604/540 |
| 2004/0261825 | A1 | * | 12/2004 | Lagace ....................... 134/95.2 |

FOREIGN PATENT DOCUMENTS

| GB | 935945 | 9/1963 | |
| JP | 2009-250264 | 10/2009 | ............ F16K 17/196 |
| KR | 10-0754134 | 8/2007 | ............ B65D 90/32 |

OTHER PUBLICATIONS

Int'l Search Report from corresponding PCT/US2011/042260 (Form PCT/ISA/210); 2 pages.

* cited by examiner

*Primary Examiner* — Michael Barr
*Assistant Examiner* — Spencer Bell
(74) *Attorney, Agent, or Firm* — Kusner & Jaffe (57) ABSTRACT

A pressure-relief assembly for adjusting pressure within a washing chamber of a washer. The pressure-relief assembly is composed of a housing having an opened upper end and an internal cavity communicating with a washing chamber of a washer. A valve assembly is moveable relative to the opened upper end of the housing between one of two opened positions and a closed position. The valve assembly has a first plate section dimensioned to overlay and cover the opened end of the housing. The first plate section has an opening extending therethrough. A second plate section is dimensioned to overlay the first plate section, the second plate section being moveable relative to the first plate section between a closed position and an open position.

17 Claims, 6 Drawing Sheets

WASHER CHAMBER PRESSURE-RELIEF ASSEMBLY

This application claims the benefit of U.S. Provisional Application No. 61/359,511 filing date Jun. 29, 2010

FIELD OF THE INVENTION

The present invention relates, generally, to a system for adjusting pressure within a region and, more particularly, to a system and assembly for equalizing pressure within a washing chamber.

BACKGROUND OF THE INVENTION

Large industrial washers are commonly used in the healthcare, pharmaceutical and scientific research industries to remove contaminants and biological waste from large articles. Such washers are often used to clean racks of animal cages or to clean healthcare and scientific equipment, such as hospital beds, wheelchairs, medical instruments, utensils, carts, instrument containers, and the like. The washers typically include a large washing chamber with a large opening for providing access to the washing chamber. A movable door seals the opening and provides access to the washing chamber to allow loading and unloading of the washing chamber with articles to be cleaned. It is not unusual for these washing chambers to be over six feet tall and several feet wide and deep to accommodate large items.

During various phases of a washing cycle, fluids (both liquid and gas, namely, air) are introduced into the washing chamber by pumps or blowers to effect washing, rinsing or drying of the articles to be cleaned. Often, the fluids used within the washing chamber are heated. The heating and cooling of fluids within the washing chamber, as well as the starting and stopping of pumps and blowers, can produce significant fluctuation in pressure within the washing chamber during the different phases of the washing cycle. More specifically, changes in temperature of liquids and gases (e.g., air) and the starting and stopping of blowers and pumps can produce either an increased pressure in the washing chamber, as compared to the surrounding environment (i.e., a positive pressure), or a vacuum within the washing chamber as compared to the surrounding environment (i.e., a negative pressure).

As will be appreciated by those skilled in the art, these variations in pressure can affect the structures, i.e., sides of a large washing chamber.

To address these fluctuations of pressure within the washing chamber, it is not unusual for large washers to employ two separate pressure-relief devices to address the expansion and depression (vacuum) that can occur within the washing chamber.

The present invention provides a pressure equalization assembly that compensates for large fluctuations of pressure within a washing chamber and provides a valve assembly that provides relief of both positive pressure and negative pressure within the washing chamber of a washer.

SUMMARY OF THE INVENTION

In accordance with a preferred embodiment of the present invention, there is provided a pressure-relief assembly for adjusting pressure within a washing chamber of a washer. The pressure-relief assembly is comprised of a housing having an opened upper end and an internal cavity communicating with a washing chamber of a washer. The opened upper end has a predetermined cross-section. A valve assembly movable relative to the opened upper end of the housing is provided. The valve assembly is movable between one of two opened positions and a closed position. The valve assembly has a first plate section and a second plate section. The first plate section is dimensioned to overlay and cover the opened upper end of the housing. The first plate section has an opening extending therethrough. The second plate section is dimensioned to overlay the first plate section. The second plate section is movable relative to the first plate section between a closed position wherein the second plate section overlays and covers the opening in the first plate section and an open position wherein the second plate section is spaced from the first plate section. A biasing device exerts a biasing force on the second plate section biasing the second plate section to the closed position wherein the second plate section overlays the first plate section and closes the opening through the first plate section. A guide section is provided for guiding movement of the valve assembly relative to the opened upper end of the housing.

In accordance with another aspect of the present invention, there is provided a washer having a washing chamber dimensioned to receive articles to be washed. An exhaust blower communicates with the washing chamber for exhausting air from the washing chamber. A pressure-relief assembly communicates with the washing chamber and the exhaust blower for adjusting pressure within said washing chamber. The pressure-relief assembly has a housing having an opened upper end and an internal cavity communicating with the washing chamber of a washer and with a conduit to the exhaust blower. The opened upper end of the housing has a predetermined cross-section. A valve assembly is movable relative to the opened upper end of the housing between one of two opened positions and a closed position. The valve assembly has a first plate section dimensioned to overlay and cover the opened upper end of the housing. The first plate section has an opening extending therethrough. A second plate section is dimensioned is to overlay the first plate section. The second plate section is movable relative to the first plate section between a closed position wherein the second plate section overlays and covers the opening in the first plate section and an open position wherein the second plate section is spaced from the first plate section. A biasing device exerts a biasing force on the second plate section biasing the second plate section to the closed position wherein the second plate section overlays the first plate section and closes the opening through the first plate section. A guide section guides movement of the valve assembly relative to the opened upper end of the housing.

An advantage of the present invention is the provision of a pressure equalization system having pressure relief means to compensate for variations in pressure within a washing chamber.

Another advantage of the present invention is the provision of a pressure equalization system as described above that can compensate for both positive and negative pressure variations within the washing chamber.

A still further advantage of the present invention is a pressure equalization system as described above that includes means for locking the pressure relief system in a position sealing the washing chamber.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
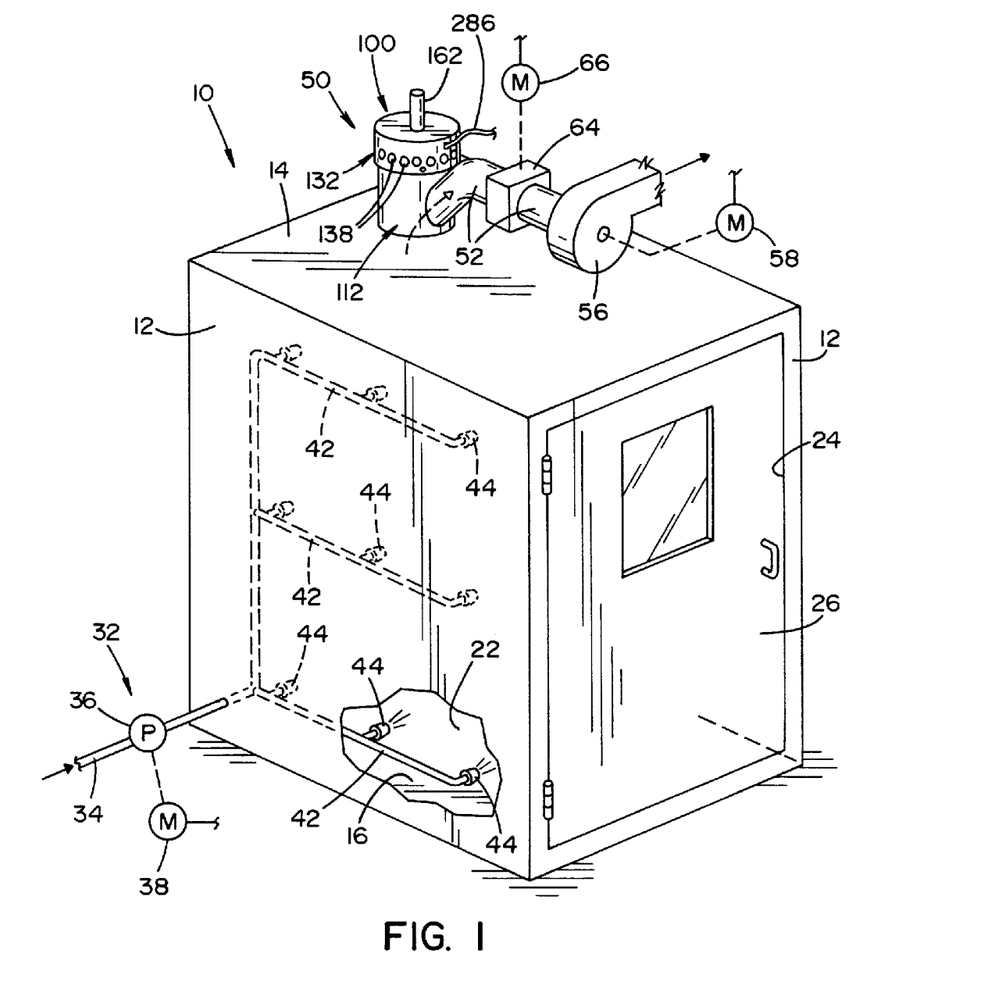
FIG. 1 is a perspective view of an industrial washer having an air exhaust assembly.

Referring now to the drawings wherein the showings are for the purpose of illustrating a preferred embodiment of the invention only and not for the purpose of limiting same, FIG. 1 schematically illustrates a washer 10 having a pressure-relief assembly 100, according to a preferred embodiment of the present invention thereon.

In the embodiment shown, washer 10 is generally rectangular in shape and includes side walls 12, a top wall 14, and a bottom wall 16 that together define a washing chamber 22. An opening 24 is formed in one of side walls 12 to provide access to washing chamber 22. Opening 24 is sealed by a movable door 26. Articles are washed within washing chamber 22 by a fluid-circulation system 32 that sprays a cleaning or decontamination fluid on the articles to be washed. In FIG. 1, only a portion of a fluid-circulation system 32 is shown for the purpose of illustration. Fluid-circulation system 32 includes a fluid inlet 34 extending through side wall 12 of washer 10. A circulation pump 36, driven by a motor 38, pumps fluids into washing chamber 22 via a plumbing network comprised of a plurality of branch conduits 42, each having a plurality of spray nozzles 44 thereon. The fluids delivered into washing chamber 22 via the plumbing network 32 are typically conventional cleaning, deactivation, and rinsing fluids. In some cases, the fluids may be heated to temperatures above room temperature. The fluids are generally collected in a sump (not shown) in the bottom of washer 10 and re-circulated through filters (not shown) back into washing chamber 22. The arrangement of plumbing network 32 within washing chamber 22 in and of itself forms no part of the present invention and has been described basically for the purpose of background information.

Figure 2:
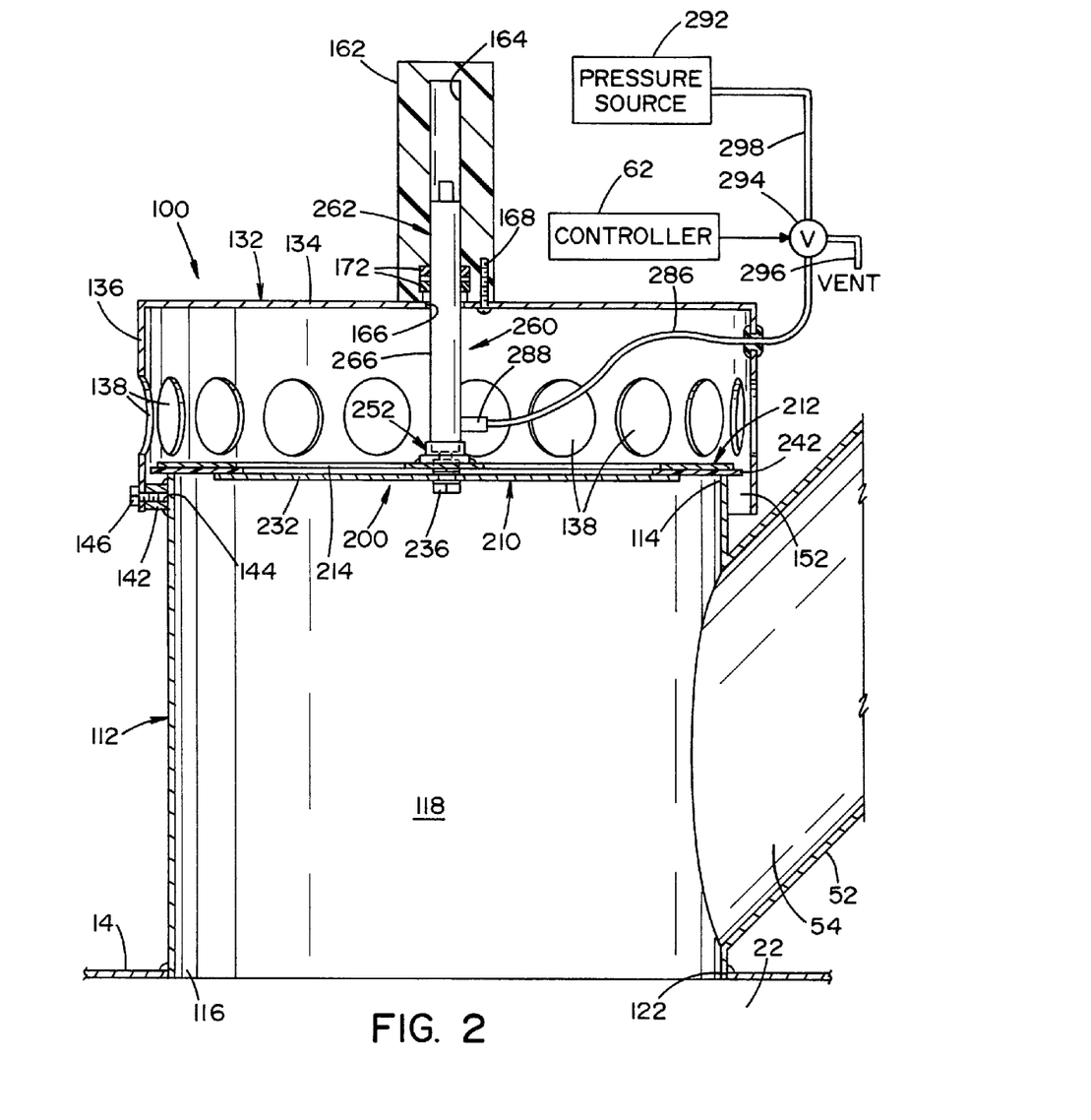
FIG. 2 is a sectional view through a portion of the air exhaust assembly shown in FIG. 1 showing a pressure relief assembly according to the present invention.

An air-exhaust assembly 50 is provided on top wall 14 of washer 10. Air-exhaust assembly 50 is comprised of a pressure-relief assembly 100, an exhaust duct 52, and an exhaust blower 56. Exhaust duct 52 defines an inner air passage 54, and extends between pressure-relief assembly 100 and exhaust blower 56. Exhaust blower 56 is driven by a motor 58 that, in turn, is controlled by a system controller 62 that is schematically illustrated in FIG. 2. Exhaust from exhaust blower 56 is directed to an air filtering and cleaning assembly (not shown) that is typically provided on washers to treat exhaust air from the washing chamber.

A damper 64 is provided within exhaust duct 52 to control air flow through air passage 54. Damper 64 is controlled by a motor 66 which, in turn, is controlled by system controller 62. Damper 64 is generally movable between an open position, allowing air flow through air passage 54 of exhaust duct 52, and a closed position, restricting air flow through air passage 54 of exhaust duct 52.

Referring now to FIG. 2, pressure-relief assembly 100 is best seen. Pressure-relief assembly 100 includes an exhaust housing 112. Exhaust housing 112 is generally tubular in shape, having an opened upper end 114 and an opened lower end 116. Exhaust housing 112 defines an inner cavity 118. Lower end 116 is secured to top wall 14 of washer 10. A hole or opening 122 in top wall 14 allows inner cavity 118 of exhaust housing 112 to communicate with washing chamber 22. As illustrated in FIG. 2, exhaust duct 52 is connected to housing 112. Air passageway 54 of exhaust duct 52 communicates with inner cavity 118 within housing 112. In the embodiment shown, housing 112 is cylindrical in shape. A cap or collet 132 is attached to upper end 114 of exhaust housing 112. In the embodiment shown, cap 132 is generally cup-shaped, having a top wall 134 and a cylindrical side wall 136 extending downward therefrom. A plurality of radially spaced-apart circular apertures 138 is formed in side wall 136 of cap 132. Mounting blocks or bosses 142 extend outwardly from the outer surface of exhaust housing 112. Blocks 142 are located near upper end 114 of housing 112, as best seen in FIG. 2. In the embodiment shown, mounting blocks 142 are generally cylindrical bosses that are welded to the outer surface of exhaust housing 112. Threaded bores 144 are formed within blocks 142 to receive conventional fasteners 146. Fasteners 146 extend through openings in side wall 136 of cap 132 to secure cap or collet 132 to upper end 114 of exhaust housing 112.

As illustrated in FIG. 2, fasteners 146 attach the lower edge of side wall 136 of cap 132 to the outward-extending mounting blocks 142 on exhaust housing 112. Cap 132 is dimensioned such that side wall 136 has a larger diameter than the diameter of exhaust housing 112, wherein a space or gap 152 exists between the outer surface of exhaust housing 112 and inner surface of side wall 136 of cap 132. As also seen in FIG. 2, cap 132 is mounted to exhaust housing 112 such that the lower end of side wall 136 extends below the upper surface of exhaust housing 112.

A centrally positioned, cylindrical housing 162 is mounted to top wall 134 of cap 132. In the embodiment shown, housing 162 is cylindrical in shape and defines a cylindrical inner bore 164 that communicates with a circular opening 166 in cap 132. Conventional fasteners 168 secure the housing to the cap. Cylindrical bore 164 of housing 162 is dimensioned to receive a rod assembly 260 of valve assembly 200, that is best seen in FIG. 2.

Figure 3:
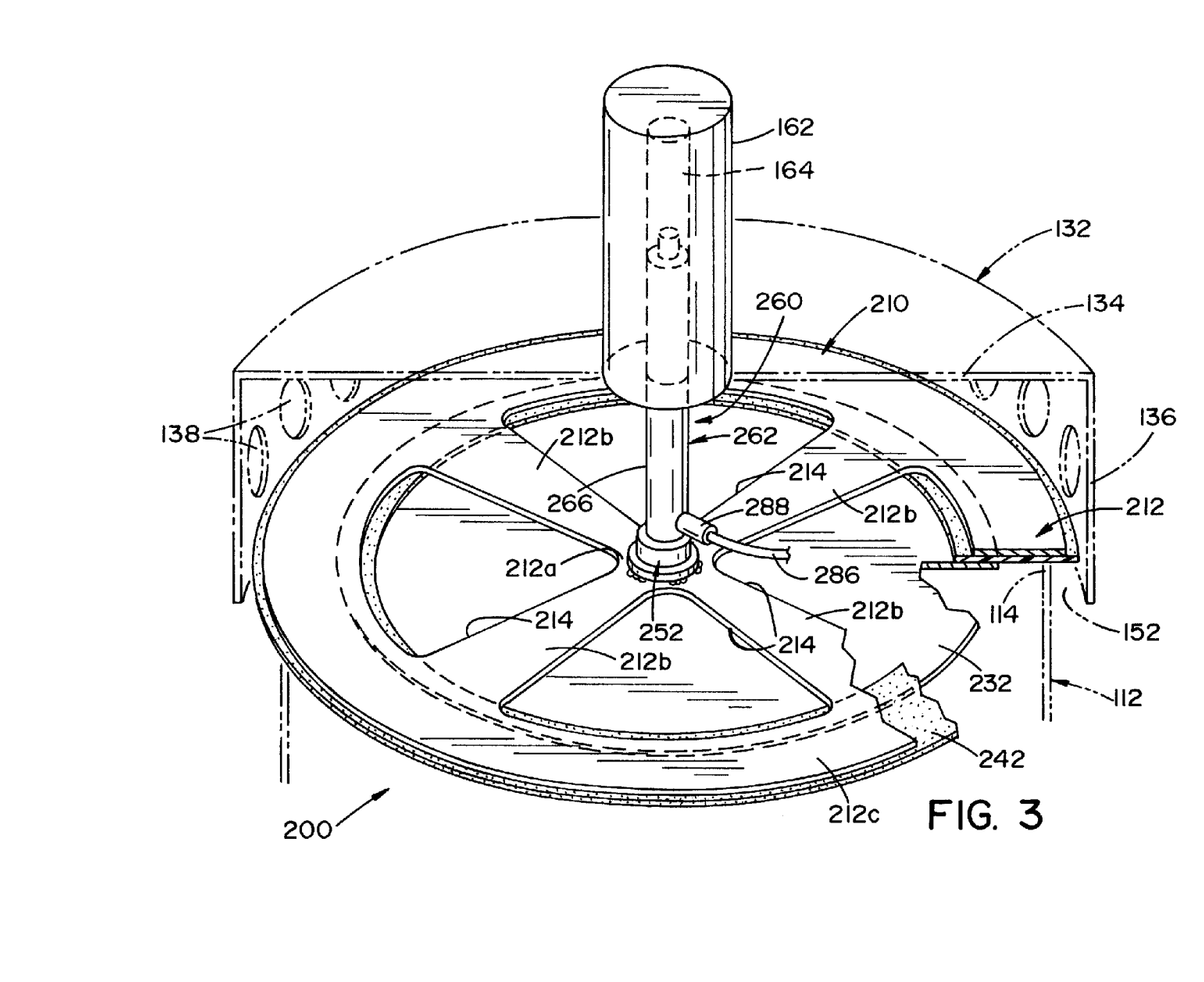
FIG. 3 is a partially sectioned, perspective view of a valve assembly that forms part of the pressure-relief assembly shown in FIG. 2.
Figure 4:
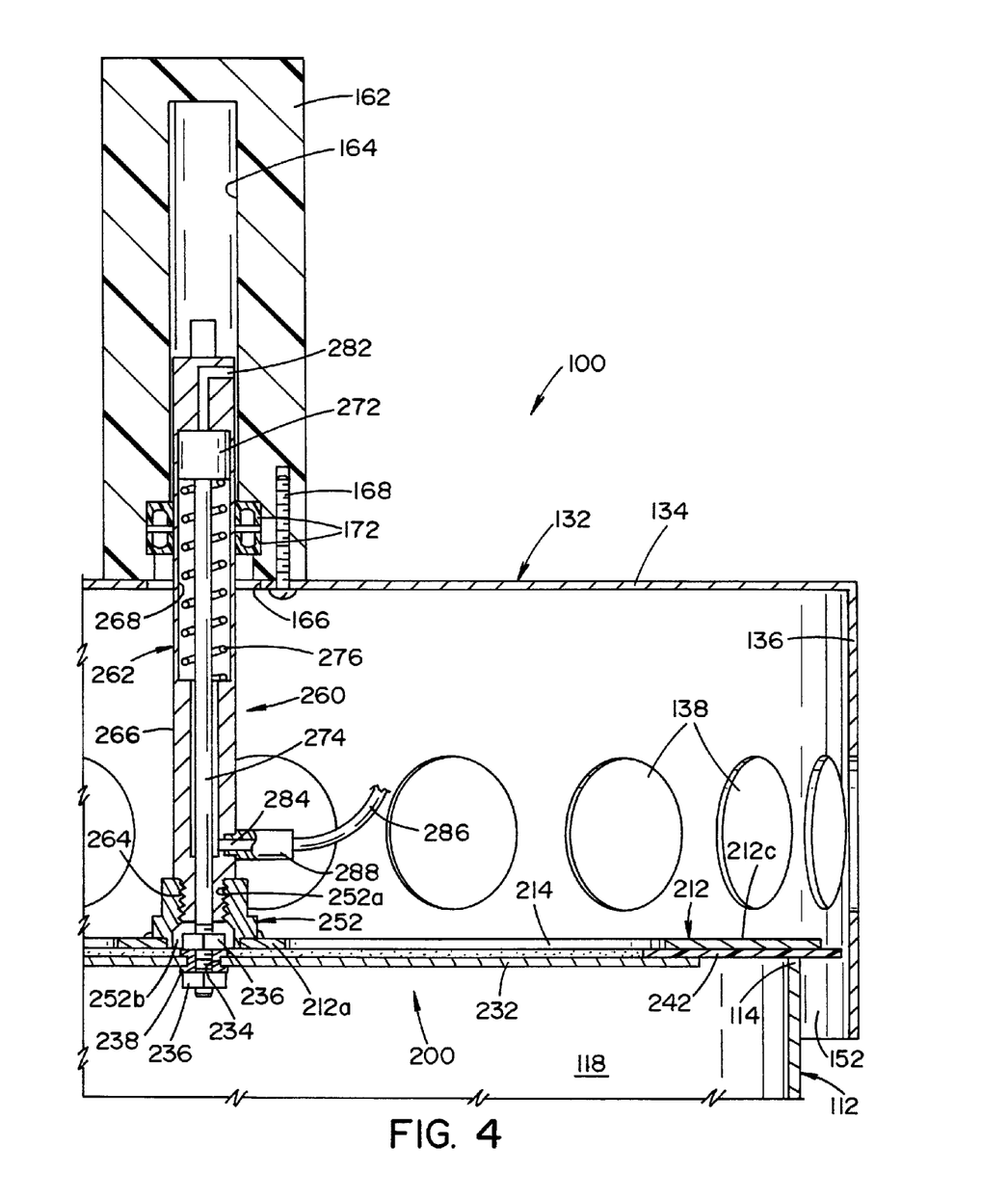
FIG. 4 is an enlarged sectional view of a portion of the pressure-relief assembly, showing the valve assembly in a neutral position when the pressure within the washing chamber is equal to the pressure of the surrounding environment.

Valve assembly 200 is generally comprised of a plate assembly 210 having rod assembly 260 extending therefrom (see FIGS. 3 and 4). Plate assembly 210 is comprised of a first plate 212, a second plate 232, and an intermediate annular seal element 242. In the embodiment shown, first plate 212 is circular and includes a central hub portion 212a. According to one aspect of the present invention, an opening 214 is formed through first plate 212. In the embodiment shown, a plurality of spaced-apart, outwardly extending leg portions 212b extend to an outer annular rim portion 212c, and a plurality of openings 214 are defined between the radially outward-extending leg portions 212b. First plate 212 is integrally formed, preferably from a flat sheet-like material. In a preferred embodiment, first plate 212 is formed from flat sheet steel. First plate 212 is generally symmetrical about a central axis and has a circular outer edge that has a dimension that is greater than the outer diameter of exhaust housing 112, but smaller than the inner diameter of side wall 136 of upper cap 132, wherein first plate 212 may rest upon upper edge of exhaust housing 112 within the area defined by side wall 136 of cap 132.

Annular seal element 242 is attached to the underside of first plate 212. As best seen in FIG. 3, annular seal element 242 is dimensioned to have a width slightly larger than the dimensions of rim portion 212c of first plate 212, such that annular seal element 242 extends beyond outer edge and inner edge of rim portion 212c of first plate 212. Annular seal element 242 is preferably formed of a resilient elastomeric or polymeric material, such as, by way of example and not limitation, neoprene or EPDM rubber.

Figure 5:
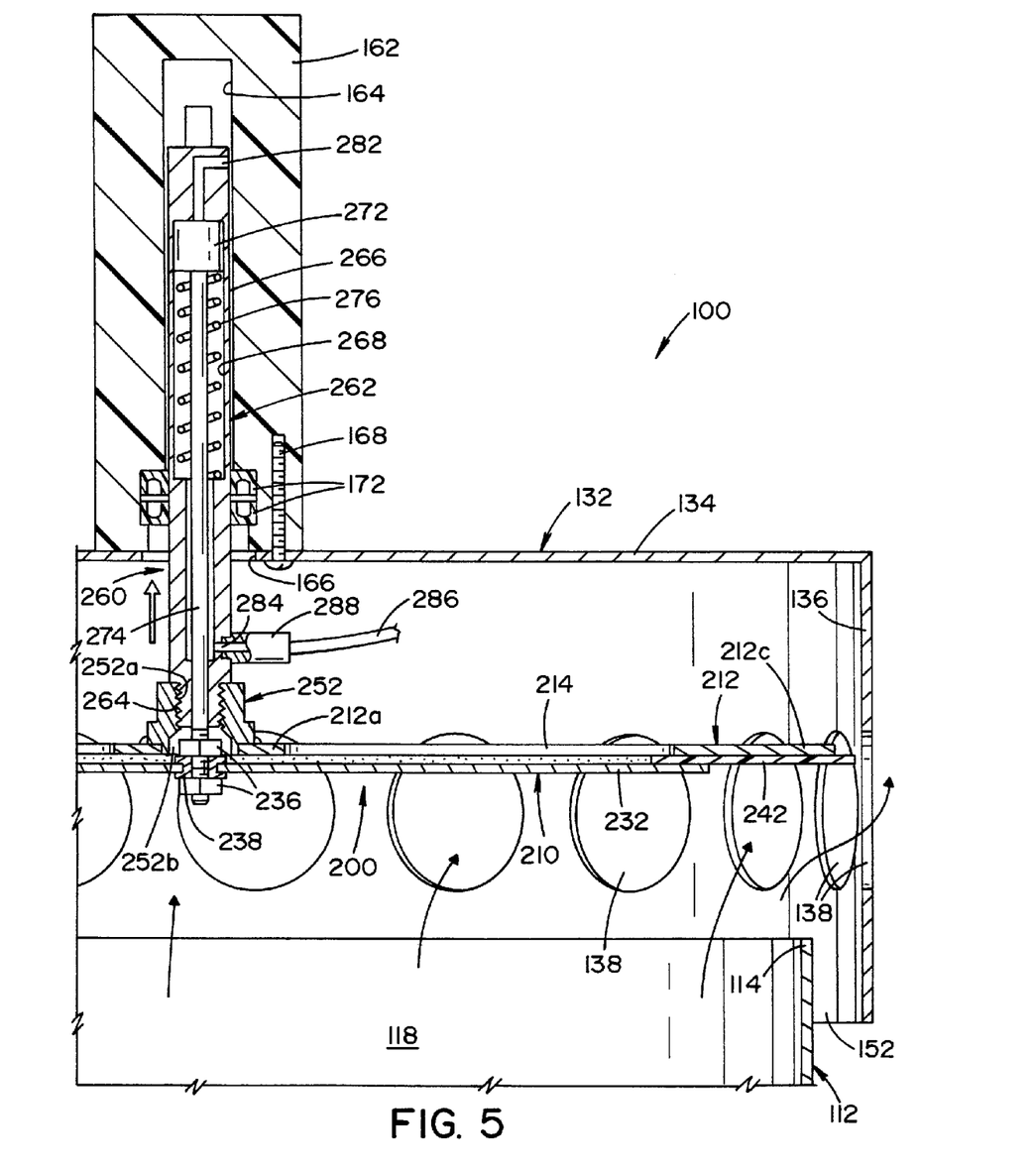
FIG. 5 is a sectional view of the pressure-relief assembly of FIG. 4, showing the valve assembly in a pressure-relieving position when the pressure within the washing chamber is above a predetermined pressure.
Figure 6:
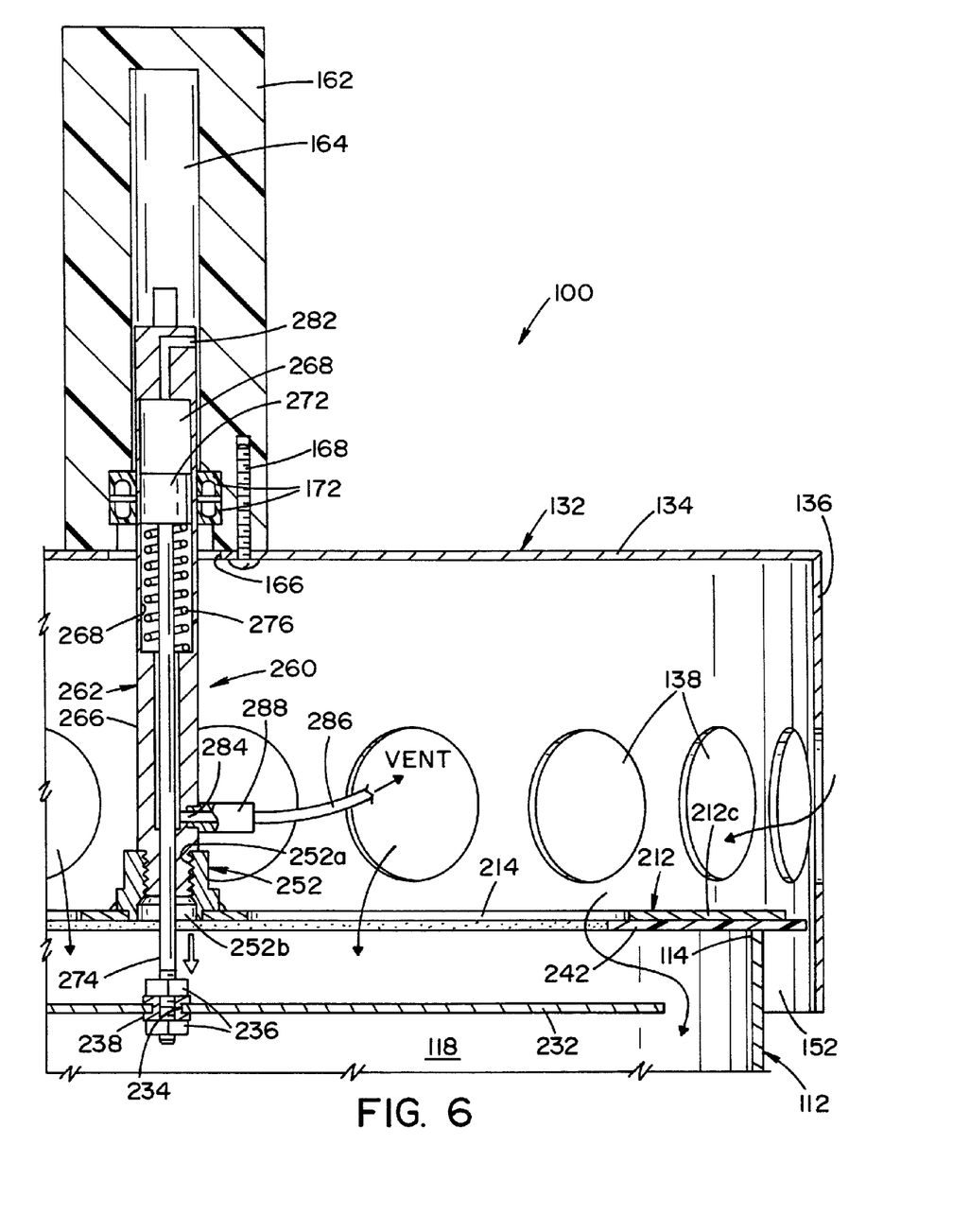
FIG. 6 is a perspective view of the pressure-relief assembly of FIG. 4, showing the valve assembly in a position when the pressure within the washing chamber is below a predetermined pressure.

A cylindrical collar 252 is centrally mounted on hub portion 212a of first plate 212, as illustrated in the drawings. A threaded bore 252a, best seen in FIGS. 4-6, extends through the upper end of collar 252. Threaded bore 252a communicates with a cavity 252b formed in the lower end of collar 252. Cavity 252b is in registry with an opening extending through the center of first plate 212, as best seen in FIGS. 4-6. Rod assembly 260 is dimensioned to be attached to collar 252. In the embodiment shown, rod assembly 260 of valve assembly 200 is an air cylinder 262. Threaded bore 252a of collar 252 is dimensioned to receive a threaded end 264 of air cylinder 262. Air cylinder 262 has an elongated cylinder housing 266. Housing 266 defines an inner piston chamber 268 dimensioned to receive a piston 272 having an elongated rod 274 that extends axially through housing 266. As illustrated in the drawings, piston rod 274 extends through the end of cylinder housing 266 and through the opening in first plate 212. A spring 276, surrounding the end of rod 274 that attaches to piston 272, is provided within cylinder housing 266 to bias piston 272 toward one end of cylinder housing 266. Air cylinder 262 includes two ports 282, 284 communicating with piston chamber 268. (These ports are typically connected to fittings that provide pneumatic pressure on opposite sides of piston 272 to move piston 272 and piston rod 274 back and forth).

In accordance with one aspect of the present invention, one end of cylinder housing 266 of air cylinder 262 is received within housing 162 attached to top wall 134 of cover 132. In this respect, housing 162 of air cylinder 266 basically becomes a guide rod within housing 162. As illustrated in FIGS. 4-6, spaced-apart gasket elements 172 form a seal around the ends of air cylinder 262. Air port 284 at the lower end of air cylinder 262 is attached to an air line 286 via fitting 288. Air line 286 from air cylinder 262 is connected to a pressure source 292 (see FIG. 2). Pressure from pressure source 292 to air cylinder 262 is controlled by a control valve 294 within the air line. Control valve 294 is controlled by system controller 62, as schematically illustrated in FIG. 2. Controller 62 controls the position of control valve 294 between a first position connecting air line 286 from air cylinder 262 allowing air cylinder 262 to be vented through line 296, and a second position connecting air line 286 from air cylinder 262 to air line 298 to pressure source 292.

As best seen in FIG. 4, rod 274 extending from piston 272 is dimensioned to extend through and beyond threaded end 264 of air cylinder 262. A circular, second plate 232 is attached to the free end of piston rod 274, as best seen in FIGS. 4-6. The free end of piston rod 274 is threaded. In the embodiment shown, second plate 232 is a flat, circular plate that has a centrally disposed opening 234 therethrough through which threaded end 264 of piston rod 274 extends. Conventional fastening nuts 236 attach lower plate 232 to the end of piston rod 274. In the embodiment shown, a spacer 238 captures the inner edge of second plate 232 and is disposed between the two fastening nuts 236 that secure plate 232 to the free end of piston rod 274.

First plate 212, intermediate annular seal element 242, and second plate 232 together form valve assembly 200 that opens and closes the upper end of inner cavity 118 based upon the pressure experienced within exhaust housing 112, i.e., the pressure within washing chamber 22. In this respect, as best seen in FIG. 4, valve element 200 is dimensioned to rest upon the upper edge of exhaust housing 112, with annular seal element 242 engaging the upper edge of exhaust housing 112. In this position, lower plate 232 is biased by spring 276 within air cylinder 262 to the position shown in FIG. 4, wherein second plate 232 engages the lower surface of annular seal element 242.

As shown in the drawings, second plate 232 is dimensioned to have an outer diameter that is smaller than the inner diameter of exhaust housing 112 and that overlaps the inner edge of first plate 212. In other words, second plate 232 is dimensioned to cover opening(s) 214 defined in first plate 212.

As best seen in FIG. 4, spring 276 within air cylinder 262 biases piston 272 and piston rod 274 toward a first end, i.e., the upper end in the drawings, of air cylinder 262, thereby forcing second plate 232 of valve assembly 200 against annular seal element 242 and the inner surface of first plate 212. In this position, second plate 232 effectively closes opening(s) 214 in first plate 212. At the same time, the weight of valve assembly 200 causes valve assembly 200 to rest upon the upper edge of exhaust housing 112 with annular seal element 242 disposed between the edge of first plate 212 and the upper edge of exhaust housing 112. Housing 266 of air cylinder 262 is free to move within cylindrical bore 164 in housing 162.

Referring now to the operation of the present invention, when washer 10 is not in use or operation, valve assembly 200 of pressure-relief assembly 100 will assume the position shown in FIG. 4, with valve assembly 200 resting on the upper edge of exhaust housing 112. In this position, the weight of air cylinder 262 and valve assembly 200 causes annular seal 242 to be pressed against the upper edge of exhaust housing 112, thereby closing the upper end of exhaust housing 112 and sealing exhaust housing 112 and, in turn, sealing washer chamber 22. Spring 276 within air cylinder 262 biases piston 272 toward the end of air cylinder 262, causing second plate 232 to be forced against the underside of annular seal element 242, thereby forming a seal between first plate 212 and second plate 232.

As previously discussed, during different phases of a washing cycle, the pressure within washing chamber 22 may vary when pumps are initiated, heated fluid is introduced into the washing chamber, or an exhaust fan is initiated. Any of these occurrences can produce a fluctuation in the pressure within washing chamber 22.

FIG. 5 illustrates operation of pressure-relief assembly 100 when the pressure within washing chamber 22 increases and exceeds a predetermined pressure level relative to the surrounding environment. In this respect, as pressure within washing chamber 22 increases, the increased pressure exerts a force on the underside of valve assembly 200. The increased pressure exerted on the underside of valve assembly 200 produces an upward force on valve assembly 200 that is based upon the pressure exerted on the underside of plate assembly 210 of valve assembly 200 and the surface area of the underside of plate assembly 210. In this respect, according to one aspect of the present invention, the dimensions of exhaust housing 112 are selected, such that a specific pressure increases in inner cavity 118 of exhaust housing 112 will produce a certain upward force on valve assembly 200 to overcome the weight of valve assembly 200, as well as overcoming the frictional resistance exerted by gaskets 172 on the outer surface of housing 266 of air cylinder 262. As indicated above, the force exerted on valve assembly 200 is based upon the surface area of the underside of plate assembly 210 and the increase in pressure exerted on the surface area of plate assembly 210. In accordance with one aspect of the present invention, the dimensions of exhaust housing 112 and valve assembly 200, i.e., first plate 212 and second plate 232, are dimensioned such that valve assembly 200 will lift upon an over pressure of about ¼" to ½" w.g. inside washing chamber 22, i.e., inside inner cavity 118 defined by exhaust housing 112. As will be appreciated by those skilled in the art, by varying the dimensions of exhaust housing 112 and the surface area on the underside of plate assembly 210, valve assembly 200 can lift off of the upper end of exhaust housing 112, based on different pressure increases within exhaust housing 112.

As valve assembly 200 lifts off of the upper end of exhaust housing 112, as shown in FIG. 5, air within washing chamber 22 is allowed to vent through apertures 138 in side wall 136 of cap 132, thereby relieving the pressure within washing chamber 22. As will be appreciated, as the pressure within washing chamber 22 dissipates, the weight of valve assembly 200 will allow valve assembly 200 to drop back onto the upper end of exhaust housing 112. As a result, the pressure within exhaust housing 112 equalizes with the surrounding environmental pressure.

FIG. 6 shows a situation where the pressure within washing chamber 22, i.e., within inner cavity 118 within exhaust housing 112, falls below the surrounding environment. In other words, FIG. 6 shows the situation where a vacuum is created within washing chamber 22. As illustrated in FIG. 6, when negative pressure is exerted on the underside of second plate 232, the external pressure above second plate 232 will exert a force on second plate 232 to push second plate 232 downward against the upward biasing force of spring 276 within air cylinder 262. Again, as indicated above, the amount of negative pressure required to cause second plate 232 downward will depend upon the surface area of the underside of second plate 232 and the compressive force of return spring 276 within air cylinder 262. As shown in FIG. 6, first plate 212 and annular seal element 242 remain in their original positions and are prevented from downward movement by the upper edge of exhaust housing 112. Thus, second plate 232 is drawn downward against the biasing force of spring 276 of air cylinder 262, which allows external air to flow through apertures 138 in side walls 136 of upper cap 132 and through opening(s) 214 in first plate 212 into washing chamber 22 to relieve the low pressure therein. Once the pressure within washing chamber 22 has equalized with the surrounding pressure, spring 276 within air cylinder 262 will cause second plate 232 to return to its original position, as shown in FIG. 4, sealing the interior of washing chamber 22.

Valve assembly 200 thus provides a single device that allows pressure compensation for both an over-pressure situation and a vacuum situation within washing chamber 22.

In accordance with another aspect of the present invention, the present invention provides a mechanism for increasing the vacuum pressure required to open, i.e., move second plate 232, which mechanism can even prevent movement of second plate 232.

In this respect, as shown in FIG. 4, the lower end of air cylinder 262 is connected to pressure source 292. Pressure source 292 may be a pressurized gas from a vessel (not shown) or a pneumatic pump (not shown). Control valve 294 is provided between pressure source 292 and air cylinder 262. System controller 62 can allow air pressure into the underside of piston 272 to increase resistance to movement of piston 272 or to prevent movement at all by essentially providing sufficient pressure on the underside of the piston 272 to overcome any potential vacuum within washing chamber 22. In this respect, washer 10 may have certain operating phases during a washing and cleaning cycle where certain chemicals are introduced into washing chamber 22, which chemicals are not to be released to the environment. In the embodiment shown, valve 294 is connected to and controlled by system controller 62, which can allow release of any pressure buildup on the underside of piston 272. As will also be appreciated, washer 10 may be programmed wherein a vacuum is drawn on the underside of piston 272 to move second plate 232 to an open position at some desirable point in a phase of the washing cycle.

The present invention thus provides a pressure-relief assembly 100 that can be operable based upon variations occurring within washing chamber 22 or one wherein operation of pressure-relief system 100 can be manually controlled by a system controller.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A pressure-relief assembly for adjusting pressure within a washing chamber of a washer, said pressure-relief assembly comprised of:

a housing having an opened upper end and an internal cavity communicating with a washing chamber of a washer, said opened upper end having a predetermined cross-section; and a valve assembly movable relative to said opened upper end of said housing between one of two opened positions and a closed position, said valve assembly having:

a first plate section dimensioned to overlay and cover said opened upper end of said housing, said first plate section having an opening extending therethrough;

a second plate section dimensioned to overlay said first plate section, said second plate section being movable relative to said first plate section between a closed position wherein said second plate section overlays and covers said opening in said first plate section and an open position wherein said second plate section is spaced from said first plate section;

a fluid cylinder having a cylinder housing, said cylinder housing having a cylindrical outer surface and containing a piston rod with a piston and a biasing element biasing said piston and piston rod, wherein said cylinder housing is connected to said first plate section, and said second plate section is connected to a free end of said piston rod, such that said second plate section is movable relative to said first plate section, and said biasing element biases said second plate section toward a closed position relative to said first plate section, wherein said second plate section overlays and covers said opening in said first plate section; and a guide section for guiding movement of said valve assembly relative to said opened upper end of said housing, said guide section including a cylindrical inner bore dimensioned to receive the cylinder housing therein, wherein said cylinder housing is movable within said inner bore.

2. A pressure-relief assembly as defined in claim 1,
wherein the weight of said valve assembly causes said valve assembly to rest upon said housing, closing said opened upper end thereof, and
wherein an over-pressure condition within said washing chamber above a predetermined level exerts a force on said valve assembly, causing said valve assembly to move off said upper end of said housing to one of said two open positions, thereby venting pressure from said chamber of said housing, and
wherein an under-pressure condition within said washing chamber below a predetermined level exerts a force on said second plate section of said valve assembly causing said second plate section to move to said open position, allowing external air to enter said washing chamber through said opening in said first plate section.

3. A pressure-relief assembly as defined in claim 2, further comprising a system for varying the under-pressure condition required to move said second plate section relative to said first plate section.

4. A pressure-relief assembly as defined in claim 1, wherein said first plate section and said second plate section are movable together from a closed position to a first of said two opened positions, when pressure within said washing chamber exceeds a predetermined pressure level.

5. A pressure-relief assembly as defined in claim 1, wherein said second plate section is movable to said open position spaced from said first plate section, when pressure within said washing chamber drops below a predetermined pressure level.

6. A pressure-relief assembly as defined in claim 1, wherein said guide section is a housing having an opening for receiving said cylinder, said cylinder being movable within said opening in said housing.

7. A pressure-relief assembly as defined in claim 1, wherein said cylinder is an air cylinder.

8. A washer, comprising:
a washing chamber dimensioned to receive articles to be washed;
an exhaust blower communicating with said washing chamber for exhausting air from said washing chamber; and
a pressure-relief assembly communicating with said washing chamber and said exhaust blower for adjusting pressure within said washing chamber, said pressure-relief assembly having:
a housing having an opened upper end and an internal cavity communicating with said washing chamber of a washer and with a conduit to said exhaust blower, said opened upper end having a predetermined cross-section; and
a valve assembly movable relative to said opened upper end of said housing between one of two opened positions and a closed position, said valve assembly having:
a first plate section dimensioned to overlay and cover said opened upper end of said housing, said first plate section having an opening extending therethrough;
a second plate section dimensioned to overlay said first plate section, said second plate section being movable relative to said first plate section between a closed position wherein said second plate section overlays and covers said opening in said first plate section and an open position wherein said second plate section is spaced from said first plate section;
a fluid cylinder having a cylinder housing, said cylinder housing having a cylindrical outer surface and containing a piston rod with a piston and a biasing element biasing said piston and piston rod,
wherein said cylinder housing is connected to said first plate section and said second plate section is connected to a free end of said piston rod, such that said second plate section is movable relative to said first plate section, and said biasing element biases said second plate section toward a closed position relative to said first plate section, wherein said second plate section overlays and covers said opening in said first plate section; and
a guide section for guiding movement of said valve assembly relative to said opened upper end of said housing, said guide section including a cylindrical inner bore dimensioned to receive the cylindrical housing therein, wherein said cylinder housing is movable within said bore.

9. A washer as defined in claim 8, wherein said first plate section and said second plate section are movable together from a closed position to a first of said two opened positions, when pressure within said washing chamber exceeds a predetermined pressure level.

10. A washer as defined in claim 8, wherein said second plate section is movable to said open position spaced from said first plate section, when pressure within said washing chamber drops below a predetermined pressure level.

11. A washer as defined in claim 8, wherein said guide section is a housing having an opening for receiving said cylinder, said cylinder being movable within said opening in said housing.

12. A washer as defined in claim 8, wherein said cylinder is an air cylinder.

13. A washer as defined in claim 8, further comprising a system for varying the under-pressure condition required to move said second plate section relative to said first plate section.

14. A washer as defined in claim 13, wherein said system exerts a force on said second plate section, said force opposing said biasing device.

15. A washer as defined in claim 14, wherein said system is a pneumatic system exerting an air pressure on said second plate section.

16. A pressure-relief assembly for adjusting pressure within a washing chamber of a washer, said pressure-relief assembly comprised of:
a housing having an opened upper end and an internal cavity communicating with a washing chamber of a washer, said opened upper end having a predetermined cross-section; and a valve assembly movable relative to said opened upper end of said housing between one of two opened positions and a closed position, said valve assembly having:
a first plate section dimensioned to overlay and cover said opened upper end of said housing, said first plate section having an opening extending therethrough;
a second plate section dimensioned to overlay said first plate section, said second plate section being movable relative to said first plate section between a closed position wherein said second plate section overlays and covers said opening in said first plate section and an open position wherein said second plate section is spaced from said first plate section;

a fluid cylinder having a cylinder housing and a piston rod movable in said fluid housing, said cylinder housing being connected to said first plate section and a free end of said piston rod being connected to said second plate section, said piston rod being biased to bias said second plate section toward a closed position relative to said first plate section;

a guide section for guiding movement of said valve assembly relative to said opened upper end of said housing;

means for selectively preventing movement of said piston rod in said cylinder; and means for selectively maintaining said first and second plate sections in said closed position.

17. A pressure-relief assembly as defined in claim 16, wherein said means for selectively preventing movement of said piston comprises applying pressure to one side of said piston rod to prevent movement of said piston rod.

* * * * *